US006552172B2

(12) United States Patent
Marx et al.

(10) Patent No.: US 6,552,172 B2
(45) Date of Patent: Apr. 22, 2003

(54) FIBRIN NANOPARTICLES AND USES THEREOF

(75) Inventors: Gerard Marx, Jerusalem (IL); Raphael Gorodetsky, Jerusalem (IL)

(73) Assignee: Habto Biotech, Inc., Garden City, NY (US)

( * ) Notice: Subject to any disclaimer, the term of this patent is extended or adjusted under 35 U.S.C. 154(b) by 0 days.

(21) Appl. No.: 09/942,984

(22) Filed: Aug. 30, 2001

(65) Prior Publication Data

US 2003/0045690 A1 Mar. 6, 2003

(51) Int. Cl.[7] .................... A61K 35/14; C12M 11/02; C12M 5/00; C07K 14/00
(52) U.S. Cl. ................ 530/382; 424/409; 424/489; 435/177; 435/182; 435/395; 530/383; 530/402
(58) Field of Search ................ 530/382, 383, 530/402; 424/409, 489; 435/177, 182, 395

(56) References Cited

U.S. PATENT DOCUMENTS

| | | |
|---|---|---|
| 3,663,687 A | 5/1972 | Evans |
| 3,937,668 A | 2/1976 | Zolle |
| 4,147,767 A | 4/1979 | Yapel, Jr. |
| 4,373,027 A | 2/1983 | Berneman et al. |
| 5,069,936 A | 12/1991 | Yen |
| 5,260,420 A | 11/1993 | Burnouf-Radosevich et al. |
| 5,324,647 A | 6/1994 | Rubens et al. |
| 5,411,885 A | 5/1995 | Marx |
| 5,635,609 A | 6/1997 | Levy et al. |
| 5,637,687 A | 6/1997 | Wiggins |
| 5,783,214 A | 7/1998 | Royer |
| 5,879,924 A | 3/1999 | Foster et al. |
| 6,150,505 A * | 11/2000 | Marx et al. .......... 530/382 |

FOREIGN PATENT DOCUMENTS

| | | | |
|---|---|---|---|
| DE | WO 01/03670 | * | 1/2001 |
| WO | PCT 94/04260 | | 3/1994 |
| WO | PCT 99/15637 | | 4/1999 |

OTHER PUBLICATIONS

Arshady, Microspheres and microcapsules: a survey of manufacturing techniques. Part I: suspension cross–linking. Polymer Engineering and Science, 29:1746–58, 1989.
Arshady, Microspheres and microcapsules: a survey of manufacturing techniques. Part II: coacervation. Polymer Engineering and Science, 30:905–914, 1990.
Arshady, Microspheres and microcapsules: a survey of manufacturing techniques. Part III: solvent evaporation. Polymer Engineering and Science, 30:915–24, 1990.
Berman et al., An early transient increase of intracellular Na+ may be one of the first components of the mitogenic signal. Direct detection by 23Na–NMR spectroscopy in quiescent 3T3 mouse fibroblasts stimulated by growth factors. Biochimica et Biophysica Acta., 1239:177–85, 1995.
Ho et al., Fibrin based drug delivery systems II. The preparation and characterization of microbeads. Drug Develop. & Indust. Pharmacy 20:535–46, 1994.
Lee et al., Serum albumin beads: an injectable, biodegradable system for the sustained release of drugs. Science, 213:233–35, 1981.
Miyazaki et al., Preparation and evaluation in Vitro and in Vivo of fibrinogen microspheres containing adriamycin. Chem. Pharm. Bull., 34:3384–93, 1986.
Senderoff et al., Fibrin based drug delivery systems. Journal of Parenteral Science and Technology, 45:2–6, 1991.
Suslick and Grinstaff, Protein microencapsulation of non–aqueous liquids. Journal of American Chemical Society, 112:7807–9, 1990.
Yapel, Jr., Albumin microspheres: heat and chemical stabilization. Methods in Enzymology, 112:3–43, 1985.
Ho et al., Fibrin–based drug delivery systems III: The evaulation of the release of macromolecules from microbeads. Journal of Controlled Disease, 34:65–70, 1995.
Dickinson and Yamamoto, Rheology of milk protein gels and protein–stabilized emulsion gels cross–linked with transglutaminas. J. Agric. Food Chem., 44:1371–77.
Miyazaki et al., Fibrinogen microspheres as novel drug delivery systems for antitumor drugs. Chem. Pharm. Bull. 34:1370–75, 1986.
Blinc et al., Atomic force microscopy of fibrin networks and plasma clots during fibrinolysis, 2000, Fibrinolysis & Proteolysis, vol. 14, pp. 288–299.*

* cited by examiner

Primary Examiner—James Ketter
Assistant Examiner—D Sullivan
(74) Attorney, Agent, or Firm—Amster, Rothstein & Ebenstein (57) ABSTRACT

The present invention provides fibrin nanoparticles having a mean diameter of 200–2000 nm. The present invention provides also methods for preparing fibrin particles of various sizes, including fibrin nanoparticles and fibrin microbeads. The present invention further provides compositions comprising fibrin particles and an agent, wherein the agent is coupled to the amine or carboxy moieties on the surface of the fibrin particles. In addition the present invention provides a composition comprising fibrin nanoparticles and an agent, wherein the agent is admixed with the fibrin nanoparticles. Still further, the present invention provides a method for introducing an agent into a cell, a method for isolating stem and/or progenitor cells from a biological sample, as well as a composition comprising fibrin particles bound to stem and/or progenitor cells.

16 Claims, 4 Drawing Sheets

Mineralized matrix (arrows) from BM cells extracted by FNP, downloaded and grown on plastic.

FIG. 4

FIBRIN NANOPARTICLES AND USES THEREOF

FIELD OF THE INVENTION

The invention relates to fibrin nanoparticles, methods for preparing fibrin particles of various sizes, including fibrin nanoparticles and fibrin microbeads, and uses thereof.

BACKGROUND OF THE INVENTION

Fibrinogen is the main structural protein of the clot and has been developed in concentrated form as a fibrin glue or sealant. Fibrinogen's structure and the biochemical mechanisms of clot formation as well as fibrin interactions with platelets have been elucidated and are well documented. Beyond hemostasis, fibrin also serves as an interim matrix to recruit cells needed for the regeneration of granulation tissue. Different cell types are drawn into the clot from the tissues surrounding the wound. Ultimately, the cells drawn into the clot secrete new collagen and other extracellular matrix (ECM) molecules.

Fibrinogen is not immunogenic within the same species, as attested by the use of pooled fibrin glue for clinical applications (Radosevich M., Goubran H. A. & Burnouf T., Fibrin sealant: Scientific rationale, production methods, properties and current clinical use. *Vox Sang.*, 72: 133–143, 1997; Marx G. Kinetic and mechanical parameters of fibrin glue. Symposium on Surgical Tissue Adhesives: Atlanta Ga. In: Current Trends in Surgical Tissue Adhesives, Sierra D. & Saltz R. (Eds) (1996)). In addition to fibrinogen's hemostatic activity, fibrin(ogen) (which is known in the art as a reference to fibrin and/or fibrinogen) has been shown to elicit cell attachment (haptotaxis) and migratory (chemotaxtic) responses with different cell types including mouse and human fibroblasts (MF & HF), bovine aortic endothelial (BAEC) and smooth muscle cells (SMC) (Gorodetsky, R., et al. *J. Lab. Clin. Med.*, 131: 269–280, 1998).

Fibrinogen is heat sensitive and becomes denatured above 50° C. By contrast, endogenous factor XIII is less heat sensitive and can induce cross-links even at higher temperatures. Based upon these properties of fibrinogen and factor XIII, the inventors devised a patented process for preparing fibrin microbeads ("FMB") (see, U.S. Pat. No. 6,150,505, issued Nov. 21, 2000). The process involved reacting fibrinogen and thrombin, in heated vegetable oil (70–80° C.) in the presence of endogenous factor XIII. The crude FMB isolated from the above procedure were filtered through fine mesh filter and sedimented in 95% ethanol. Microscopic evaluation indicated that the FMB were 50–200 µm in diameter (Gorodetsky, et al., *J. Invest. Dermatol.*, 112(6): 866–872, June 1999). Tests with sucrose solutions indicated that the FMB have a density 1.32+0.1 gm/ml.

The FMB offered a significant improvement over fibrin microbeads of the prior art. Specifically, since factor XIII was used as the cross linking agent rather than exogenous chemical cross linking agents, such as glutaraldehyde (which was typically used in the preparation of fibrin beads (see, Ho, et al., *Drug Dev. and Ind. Pharm.* 20(4):535–546, 1994)), the FMB retained the haptotactic and chemotaxtic properties of fibrin(ogen) for a variety of cell types. It is believed that the use of exogenous chemical cross linking agents, such as glutaraldehyde, not only destroys certain biologically active sites, thereby interfering with the binding of the microbeads to cells, but also may render the microbeads immunogenic.

In addition, it is believed that the combination of heat and factor XIII in the preparative process of the FMB allowed a significantly greater degree of cross-linking of the fibrin (ogen) than would otherwise occur in physiologic fibrin, or fibrin-based drug delivery systems such as described in Senderoff, et al., (*J. Parenteral Sci. & Tech.*, 45(1): 2–6, 1991). This renders the FMB stable for prolonged periods in aqueous solution, a property that is particularly desirable for use as vehicles for culturing cells, as well as for other uses.

SUMMARY OF THE INVENTION

The present invention is directed to fibrin nanoparticles (FNP) having a mean diameter of 200–2000 nm. The FNP of the present invention, like the FMB of U.S. Pat. No. 6,150,505, do not contain any exogenous cross-linking agents such as glutaraldehyde that can damage certain biologically active sites and affect the rate of their enzymatic degradation, and therefore FNP are reactive with various types of cells. Rather, the FNP of the present invention are prepared by reacting fibrinogen, thrombin and Factor XIII under heat, where the Factor XIII acts as the cross-linking agent. As a result of the preparation process, the FNP of the present invention contain extensive cross-linking of fibrin (ogen), which renders the fibrin particles stable for prolonged periods in aqueous solution.

However, it has been unexpectedly found that the FNP of the present invention, unlike the larger FMB, are taken up into the cytoplasm of cells. Therefore, the FNP of the present invention offers an innovative and unique solution for selectively delivering agents into cells, including agents that are not normally taken up by cells. Since the FNP of the present invention are also non-toxic, minimally non-immunogenic and biodegradable, FNP is a significant advancement in the field of drug delivery.

In addition to FNP, the present invention also provides a method for preparing FNP comprising the steps of: (i) mixing an aqueous solution comprising fibrinogen, thrombin and Factor XIII in an oil emulsion at a temperature of 50–80° C., without the addition of an exogenous chemical cross-linking agent, until fibrin microbeads are formed in the mixture; (ii) homogenizing the mixture to form FNP having a mean diameter of 200–2000 nm in the mixture; and (iii) isolating FNP having a mean diameter of 200–2000 nm from the mixture.

In addition, the present invention provides another method for preparing fibrin particles of any size. This method is comprised of the steps of: (i) mixing an aqueous solution comprising fibrinogen, thrombin and Factor XIII, without the addition of an exogenous chemical cross-linking agent, in a manner to obtain a fibrin clot; (ii) incubating the fibrin clot at ambient temperature for a period of time sufficient to obtain a cross-linked fibrin clot; (iii) mixing the cross-linked fibrin clot in oil at a temperature of 50–80° C. to obtain dehydrated fibrin pieces; (iv) homogenizing or grinding the fibrin pieces to obtain fibrin particles of the desired size; and (v) isolating the fibrin particles of the desired size. This method may be used to prepare particles of any size, including FNP and FMB.

The present invention also provides another method for preparing fibrin particles of any size. This method comprises the steps of: (i) mixing an aqueous solution comprising fibrinogen, thrombin and Factor XIII, without the addition of an exogenous chemical cross-linking agent, in a manner to obtain a fibrin clot; (ii) incubating the fibrin clot at ambient temperature for a period of time sufficient to obtain a cross-linked fibrin clot; (iii) heating the cross-linked fibrin clot at a temperature of 50–80° C. to obtain fibrin pieces; (iv) homogenizing the fibrin pieces to obtain fibrin particles of the desired size; and (v) isolating the fibrin particles of the desired size. This method also may be used to prepare FNP, FMB and fibrin particles of other sizes.

The present invention provides yet another method for preparing fibrin particles of any size, that comprising the steps of: (i) introducing an aqueous solution comprising fibrinogen, thrombin and Factor XIII, without the addition of an exogenous chemical cross-linking agent, into a spray dryer; (ii) spray drying the mixture to obtain spray dried fibrin particles; (iii) heating the spray dried particles at a temperature of 50–80° C. to dehydrate or remove water; and (iv) isolating fibrin particles of the desired size. Here again, this method may be used to prepare fibrin particles of various sizes, including FNP and FMB.

Still further, the present invention provides a composition comprising fibrin nanoparticles and an agent, wherein the agent is admixed with the fibrin nanoparticles.

In addition, the present invention provides a composition comprising fibrin particles and an agent, wherein the agent is coupled to the amine or carboxy moieties on the surface of the fibrin particles. The fibrin particles may be of any size, including FNP and FMB.

Also provided by the present invention is a method for coupling an agent to a fibrin particle comprising contacting the fibrin particle with the agent under conditions permitting the formation of a complex between the agent and the fibrin particle, and isolating the complex. Here again, the fibrin particles may be of any size, including FNP and FMB.

In addition, the present invention provides a method for introducing an agent into a cell comprising contacting the cell with a composition comprising fibrin nanoparticles and an agent, wherein the agent is admixed with the fibrin nanoparticles or coupled to the amine or carboxy moieties on the surface of the fibrin nanoparticles, so that the nanoparticles and the agent are introduced into the cell.

The present invention also provides a method for isolating stem and/or progenitor cells from a biological sample comprising stem and/or progenitor cells, said method comprising contacting the biological sample with fibrin particles so that the fibrin particles bind to the stem and/or progenitor cells present in the biological sample, and isolating the fibrin particles bound to the stem and/or progenitor cells from the biological sample.

Still further, the present invention provides a composition comprising fibrin particles bound to stem and/or progenitor cells.

Additional objects will be apparent from the description that follows.

DETAILED DESCRIPTION OF THE INVENTION

The present invention is directed to fibrin nanoparticles (FNP) having a mean diameter of 200–2000 nm. The FNP of the present invention are also characterized as being prepared by the reaction of fibrinogen, thrombin and Factor XIII under heat, where the Factor XIII acts as the cross-linking agent instead of exogenous cross-linking agents such as glutaraldehyde. In the preferred embodiment, the FNP have a density of 1.32±0.2 g/mL. The FNP are also dehydrated and comprise cross-linked fibrin(ogen), and preferably extensively cross-linked fibrin(ogen). Still further, the FNP of the present invention are biologically active.

As used herein, "biologically active" means that the FNP possess biologically active sites that permit the FNP to attract and incorporate into various types of cells. This is different than fibrin microbeads of the prior art that are treated with exogenous cross-linking agents, such as glutaraldehyde, which render such fibrin microbeads unattractive to cells, and biologically inactive and less degradable.

"Extensively cross-linked" means that the fibrin(ogen) contains at least 30% cross-linked fibrin(ogen), and more preferably at least 50% cross-linked fibrin(ogen) $\alpha$ and $\gamma$ chains. The extensive cross-linking of the FNP of the present invention is believed to occur during their manufacture, which utilizes high temperatures that help denature the native fibrin(ogen) structure, specifically the D-domain, thereby exposing sites for cross-linking by factor XIII, which are not normally cross-linked by native conformers of fibrin(ogen) at ambient temperatures. The SDS-PAGE gel patterns set forth in FIG. 1 of U.S. Pat. No. 6,150,505 for FMB show extensive cross-linking due to such factor XIII mediated reactions. It is believed that similar extensive cross-linking also renders the FNP of the present invention insoluble and stable in an aqueous environment, as well as in organic solvents, thus rendering the FNP stable when stored in ethanol or equivalent solutions or when prepared in aqueous solutions for delivering agents to cells, and for other uses.

Unless indicated otherwise, the fibrin particles prepared using the methods of the present invention have the same properties of the FNP described above, although the fibrin particles may be of any size.

Unless indicated otherwise, "FNP" refers to fibrin particles having a diameter of 20–2000 nm, while "FMB" refers to fibrin particles having a diameter of 30–300 $\mu$m.

The FNP may be prepared by four basic processes, which are referred hereafter as the 1) Fibrin/Oil Emulsion; 2) Fibrin/Oil; 3) Fibrin/Dry; and 4) Fibrin/Spray Drying/Heating processes. The Fibrin/Oil Emulsion process is similar to the process described in U.S. Pat. No. 6,150,505, which is hereby incorporated by reference in its entirety. The Fibrin/Oil, Fibrin/Dry and Fibrin/Spray Drying/Heating processes also may be used to prepare fibrin particles of various sizes, including FNP and FMB. Specifically, each process is described further below.

In this regard, in the Fibrin/Oil Emulsion process, an aqueous solution comprising fibrinogen, thrombin and factor XIII is prepared. This solution may be prepared by combining fibrinogen containing endogenous factor XIII with thrombin, by combining cryoprecipitate containing endogenous fibrinogen and endogenous factor XIII with thrombin, or by combining fibrinogen, factor XIII and thrombin individually into an aqueous solution. The heat-drying process also includes additional cross-links due to condensation reactions. It also is within the confines of the present invention that equivalent proteases such as snake venom proteases (e.g. reptilase) may be used as an alternative to thrombin. The ratio of fibrinogen:thrombin: factor XIII in the aqueous solution is preferably 5–100 mg/mL:1–100 U/mL:1–50 U/mL, and most preferably 20–40 mg/mL:5–10 U/mL:2–20 U/mL. In addition to these proteins, the aqueous solution also may contain fibronectin and other blood-derived proteins that may be present in cryoprecipitate starting materials in the course of the fibrinogen isolation. If it is desired for the FNP to contain any agents as discussed later below, then those agents can be added into the fibrinogen or thrombin solutions prior to their mixing, or directly to the aqueous solution.

Next, prior to the onset of substantial coagulation, the aqueous solution is introduced into oil heated to a temperature in the range of about 50–80° C. while being mechanically stirred to form an emulsion. A hydrophobic organic solvent such as isooctane also may be included in the oil. The inventors have found that using the concentrations of fibrinogen and thrombin in Example 1 below, coagulation usually occurs at about 10–45 seconds after the fibrinogen and thrombin are combined. However, for other concentrations of fibrinogen and thrombin, the onset of coagulation can be determined by using known coagulation assays.

Suitable oils include but are not limited to vegetable oils (such as corn oil, olive oil, soy oil, and castor oil), petroleum based oils, silicone oils, mineral oils and combinations thereof. While most oil is removed during the processing steps, vegetable oils are preferred because since any residual vegetable oil can be metabolized by cells. In the most preferred embodiment, the oil is corn oil. The inventors believe that oils that contain unsaturated bonds (i.e. Canola oil) should be avoided since they may be oxidized.

After the aqueous solution is introduced into the heated oil, the emulsion is then maintained at a temperature of about 50–80° C. and mixed at an appropriate speed until fibrin microbeads (and nanoparticles) comprising extensively cross-linked fibrin(ogen) are obtained in the emulsion. The mixing speed will depend upon the volume of the emulsion, and the desired size of the particles. For volumes of 400 mL oil and 100 mL aqueous phase in a 1 L flask, the preferred mixing speed is 300–500 rpm. The emulsion is generally mixed for about 3–9 hours, although the actual time will vary depending upon the temperature, air flow, the concentration of the initial reactants and the volume of the emulsion. As discussed above, it is believed that at temperatures of about 50–80° C., the native fibrin(ogen) structure partially denatures exposing sites for cross-linking by factor XIII, which are not normally cross-linked at ambient temperatures. Such cross-linking occurs during the first phase of the mixing/heating cycle. The heating also serves the purpose of dehydrating the matrix (drying process) thereby producing discrete cross-linked fibrin(ogen) particles that do not stick together or coalesce, as such particles do when they possess too much water.

After harvesting from the oil, washing with solvents to remove oil, and air dried, the solid particles (matrix) are then homogenized or ground using a grinder set to its "fine" settings, a milling device or mortar or pestle to obtain FNP having a mean diameter of 200–2000 nm in the mixture. Preferably, the FNP are separated by passing the mixture though a filter or sieve which allows passage of less than 20 microns. The FNP are subsequently separated from larger particles by a combination of techniques including filtration through fine mesh filters and/or differential sedimentation in alcohol or other liquids in which larger particles are sedimented by gravity and residual floating FNP are centrifuged, and collected. Preferably, the passed particles are suspended in 95% ethanol and shaken. The material which settles within 60 seconds is removed. The FNP in the supernatant are then isolated further by filtration or centrifugation. The FNP size can be determined using a Coulter particle counter or microscope.

In the Fibrin/Oil process, an aqueous solution comprising fibrinogen, thrombin and Factor XIII, without the addition of an exogenous chemical cross-linking agent, is mixed in a manner to obtain a fibrin clot. Specifically, the fibrin clot can be obtained by shaking the aqueous solution vigorously. The aqueous solution comprising the fibrinogen, thrombin and Factor XIII is prepared in the same manner as in the Fibrin/Oil Emulsion process, and may include an agent if so desired. In order to increase the foaming action of the material, the fibrinogen also may be shaken before being mixed with the additional materials. The fibrin clot is then incubated at ambient temperature for a period of time sufficient to obtain a cross-linked fibrin clot. The inventors have found that an incubation period of about 45 minutes to about 6 hours is sufficient. Next, the cross-linked fibrin clot is mixed with oil at a temperature of 50–80° C. until denature and dried fibrin pieces are obtained. The oil and the duration of mixing (i.e., about 3–9 hours) is accomplished in a similar manner as described above for the Fibrin/Oil Emulsion process. The particles of fibrin are then washed with solvent to remove residual oil, and homogenized or ground to obtain fibrin particles of the desired size, which may be isolated further by filtration, sedimentation and/or centrifugation. Specifically, FNP having a mean diameter of 200–2000 nm may be obtained using the same grinding and size separation procedures as discussed above with respect to the Oil Emulsion process. FMB of about 30–300 $\mu$m may be obtained by isolating the particles which settled in 95% ethanol after 10–20 seconds, and using a wire mesh to select for FMB of 30–300 $\mu$m in diameter.

In the Fibrin/Dry process, an aqueous solution comprising fibrinogen, thrombin and Factor XIII, without the addition of an exogenous chemical cross-linking agent, is first mixed in a manner to obtain a fibrin clot. Here again, the aqueous solution comprising the fibrinogen, thrombin and Factor XIII is prepared in the same manner as described above, and may include an agent if so desired. The fibrin clot is then incubated at ambient temperature for a period of time sufficient to obtain a cross-linked fibrin clot. An incubation period of about 45 minutes to about 2 hours is usually sufficient. Next, the cross-linked fibrin clot is heated at a temperature of 50–80° C. in a vacuum oven for a time period necessary to obtain a dehydrated matrix (about 3–9 hours). The particles of the fibrin matrix are then homogenized to obtain particles of the desired size. The desired particles, including FNP, FMB, or other particles, may be isolated using the same procedures as discussed above.

In the Fibrin/Spray Drying/Heating process, the aqueous solution comprising fibrinogen, thrombin and Factor XIII, without the addition of an exogenous chemical cross-linking agent, is first introduced into a spray dryer. Suitable spray dryers include the Buchi spray dryer, and other commercially available spray dryers. Preferably, the material is spray dried at the following parameters: feed temperature 37° C., inlet temperature 150–230° C., outlet temperature 85–120° C. and spray pressure 3 mbarr. The spray dried fibrin particles are preferably collected in a cyclone trap or similar device. The spray dried particles are then heated at a temperature of 50–80° C. to remove water. The fibrin particles of the desired size, including FNP, FMB, or other particles, may isolated using the same procedures as discussed above.

The present invention also provides a composition comprising fibrin nanoparticles and an agent, wherein the agent is admixed with the fibrin nanoparticles. In this regard, the agent may be admixed with the fibrin nanoparticles if the agent is included in the aqueous solution comprising fibrinogen, thrombin and Factor XIII (or one of its components such as fibrinogen) in the process of preparing the FNP. The resultant FNP would contain the agent which would be released upon the bio-degradation of the FNP.

The present invention also provides a composition comprising a fibrin particle of any size, including FNP and FMB, and an agent, wherein the agent is coupled to the amine or carboxy moieties on the surface of the fibrin particles. In this regard, the agents (e.g., peptides, proteins, glycoproteins, haptens or drugs) could be coupled to the FNP by surface chemistry, such as using cross-linking reagents to couple the desired ligand to the FNP, as by linking through their carboxy or amine groups.

Suitable agents include but are not limited to drugs, proteins, peptides, nucleic acids, antigens, haptens, neurologics, vitamins, vitamin derivatives, growth factors, glucocorticosteroids, steroids, antibiotics, antibacterial compounds including bacteriocidal and bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins and fragments thereof, dyes, radiolabels, radiopaque compounds, fluorescent compounds, fatty acid derivatives, saccharides, polysaccharides, cell receptor binding molecules, antiinflammatories, antiglaucomic compounds, mydriatic compounds, anesthetics, and the like. As used herein, agents also include alginate, biodegradable polymers, polyethylene glycols, sugars, and matrix components or molecules.

The present invention also provides a method for introducing an agent into a cell comprising contacting the cell with a composition comprising fibrin nanoparticles and an agent, wherein the agent is admixed with the fibrin nanoparticles or coupled to the amine or carboxy moieties on the surface of the fibrin nanoparticles, so that the nanoparticles and the agent are introduced into the cell. Here again, the agent may be a drug, protein, peptide, nucleic acid, saccharide, antigen or hapten. Suitable cells include primary endothelial cells, smooth muscle cells, dendritic cells (antigen presenting cells), fibroblasts, chondrocytes and osteoblasts, osteogenic bone marrow derived progenitors, 3T3 carcinoma cell line and mouse mammary carcinoma cell line.

The present invention also provides a method for isolating stem and/or progenitor cells from a biological sample comprising stem and/or progenitor cells. The method comprises the steps of: contacting the biological sample with fibrin particles so that the fibrin particles bind to the stem and/or progenitor cells present in the biological sample, and isolating the fibrin particles bound to the stem and/or progenitor cells from the biological sample. In this method, the biological sample may be any biological sample that contains stem and/or progenitor cells, including bone marrow, placental blood and cord blood. The fibrin particles may be of any size, but are preferably FMB having a diameter of 30–300 $\mu$m. The fibrin particles may be contacted with the biological sample in culture containing known components that are required for the maintenance and well being of stem and/or progenitor cells. At the desired time after contact, the fibrin particles bound to the stem and/or progenitor cells may be removed from the culture, and introduced into another environment for further study or manipulation. It is also within the confines of the present invention that the stem and/or progenitor cells may be removed from the fibrin particles, if desired.

The present invention is described in the following Examples which is set forth to aid in an understanding of the invention, and should not be construed to limit in any way the invention as defined in the claims which follow thereafter.

EXAMPLE 1

Preparation of FNP by Fibrin Oil Emulsion Process

An oil emulsion process similar to that used for preparing FMB (U.S. Pat. No. 6,150,505) may be used to prepare crude product. In this regard, 500 mL vegetable oil (corn, soya, castor) is heated to 60–75° C. with stirring at 350 rpm. A mixture of fibrinogen (25 mg/ml) and thrombin (5 U/ml), which has not yet clotted is then added to the hot oil. The aqueous droplets of fibrin will continue to cross-link due to the activity of the endogenous factor XIII. After 4–6 hours, the resultant solid particles are collected, washed with hexane and acetone to remove oils and air dried (yield 1.1 gm). This results in the formation of FMB and residual FNP are centrifuged and collected as "fine". To increase the proportion of yield of FNP, the larger FMB can be ground, as follows.

Grinding Step: This crude FNB product contains a heterogeneous collection of particles from 10 to 300 micron in diameter. In order to reduce particle size, the entire mixture is subjected to grinding through a grinder set to its "fine" settings, or subjected to a milling device or mechanically ground with a mortar and pestle or alternative devices.

Size Separation Step: The resultant powder is separated into different size particles by passing through a series of sieves. The smallest particles passing through a sieve which allows passage of less than 20 microns are suspended in 95% ethanol and shaken. The material that settles within 120 seconds is removed and the supernatant contains FNP. For further removal of larger particles the ethanol solution with FNP is centrifuged to sediment and collect all FNP, whose size can be determined in a Coulter particle counter or in a microscope (i.e. 200–2000 nm mean diameter).

EXAMPLE 2

Preparation of FNP by Fibrin/Oil Process

Coagulation step: 25 ml fibrinogen (40 mg/ml) is introduced into a 50 ml capped test tube, and shaken vigorously to ensure much bubbling. 1 ml thrombin (400 U/ml) is added and the mixture is stirred vigorously to achieve clotting within about 0.5 minute. The entire mixture becomes a clot. The mixture is then allowed to set for 1 hour at ambient temperature to ensure good cross-linking.

Oil step: The fibrin clot is then removed, broken up into smaller particles and placed into vegetable oil (500 ml corn, soya or castor oil) heated to 60–70° C. with stirring at 30–80 rpm. The large fibrin pieces can then be broken up into smaller pieces. The heating then continues with slow stirring (~20 rpm) at around 75° C. for 4–6 hours. The resultant dehydrated condensed fibrin pieces are collected, washed with hexane and acetone to remove oils and air dried (crude yield: 2.4 gm). The resultant dehydrated fibrin matrix is then subjected to the grinding and size separation steps described in Example 1.

EXAMPLE 3

Preparation of FNP by Fibrin/Dry Process 25 ml Fibrinogen (40 mg/ml) is mixed in a 50 ml capped test tube, and 1 ml thrombin (400 U/ml) is added. The mixture is then shaken gently and poured onto a non-sticking parafilm sheet, and clotting is achieved in about 1 minute. The mixture is then allowed to sit for about 1 hour to achieve good cross-linking. The material is then broken up with a spatula. The pieces are then placed on aluminum foil, and heated in a vacuum oven at 60–70° C. After a few hours, the chunks of fibrin clot dehydrates and hardens. If the starting mixture of fibrinogen and thrombin contains heat labile additives, it is suggested that the fibrin chunks be heated in a vacuum oven below 50° C. in order to retain activity of the heat labile additives. Following the dehydration step, the pieces of the fibrin clot are then subjected to the grinding and size separation steps described in Example 1.

EXAMPLE 4

Preparation of FNP by Fibrin/Spray Drying/Heating Process

Fibrinogen (25 mg/mL) was mixed with thrombin (20 U/mL) for 20 sec, and the still fluid mixture was injected into a spray dryer (Buchi spray drier; feed temperature 37° C., inlet temperature 150–230° C., and outlet temperature 85–120° C.). The particulates were collected in a cyclone trap using the following spray-dry parameters: chamber temperature 150–230° C., outlet temperature: 85–120° C., and spray pressure: 3 mbarr. The powder obtained in the cyclone trap was then cured in an oven at 80° C. for 6 hours to remove water. Subsequently, the powder was then suspended in 95% ethanol and shaken. The material which settled within 60 seconds was removed and the supernatant contains FNP, whose size can be determined as described in Example 1.

EXAMPLE 5

Characterization of FNP

FNP Solubility. The FNP were tested for solubility in Tris/saline or in 4 M urea monitored by phase contrast microscopy. Neither the Tris buffer nor the 4 M urea dissolved FNP for up to 1 week at room temperature.

SDS-PAGE. FNP were partially digested in 0.1 N NaOH, and subjected to reduced 4–12% gradient SDS-PAGE (Nova, Encino, Calif.), with fibrinogen or normally clotted fibrin as controls. Results indicate the FNP are extensively cross-linked.

FNP Density. FNP were prepared in our laboratory and were subjected to sucrose density sedimentation for density evaluation. The preparations we made were found to exhibit a density of about 1.32±0.2 g/ml.

Figure 1:
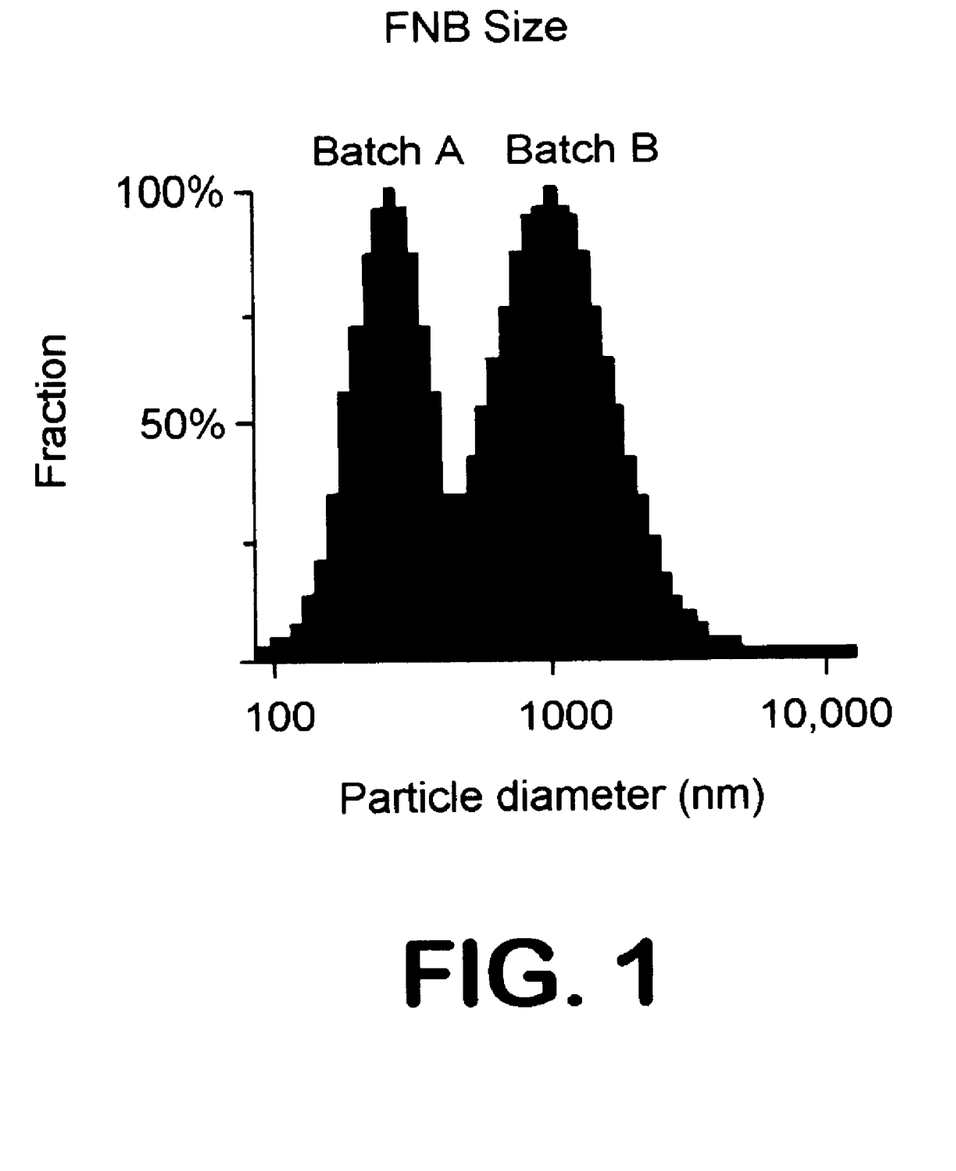
FIG. 1. Size distribution of two batches of FNP, with mean particle diameters of 305 and 994 nm, respectively.

FNP Size. Coulter sub-micron particle analyzer indicated that different batches of FNP exhibited a mean diameter in the range 200–995 nm. Size distribution of two batches of FNP, with mean particle diameters of 305 and 994 nm, respectively, is shown in FIG. 1.

EXAMPLE 6

Derivatization of FNP

The FNP were derivatized through their surface amine ($NH_2$) groups as follows: FNP (100 μl packed volume) were suspended in 2 mL carbonate buffer, pH 8.2 with 2 mg fluorescein isothiocyanate (FITC) and incubated with stirring for 2 hrs at ambient temperature in the dark. The reaction was stopped by adding 100 μL Tris/saline buffer and the particulates isolated by centrifugation and disaggregated by mixing and sonication. The resultant FITC-FNP were highly fluorescent.

Protein was coupled to the FNP by employing a water soluble carbodiimide reagent 1-Ethyl-3(3-Dimethylaminopropyl)carbodiimide Hydrochloride (EDC) (MW 191.7, Pierce Co.) as follows: Packed FNP (100 μL) suspended in 2 mL conjugation buffer (0.1 M MES (2-[N-morpholino]ethane sulfonic acid), pH 4.5–5). FITC-albumin (100 μL, 2 mg/mL) was added and the mixture stirred on an orbital shaker. EDC (2 mg) was added and the entire mixture was shaken at ambient temperature for 2 hours. The reaction was stopped by adding 100 μL Tris/saline buffer. The particulates were isolated by centrifugation at 3000 rpm, and disaggregated by mixing and sonication. On the basis of the residual OD 280 of the supernatant, more than 70% of the FITC-protein became coupled to the FNP. Other coupling chemical reactions are also known and could be used to bind different groups or proteins to FNP (or FNB and fibrin particles of other sizes).

Using similar chemistry to the one used for coupling FITC or FITC-albumin, other proteins or polymers or antigens may be coupled to the surface of the FNP. Alternatively, other cross-linking reagents such as gluteraldehyde may be employed to couple materials onto the surface of the FNP. Other cross-linking reagents known to those skilled in the art may also be employed. FNP may also be derivatized with protein (or hapten) by adding the protein (or hapten) to the fibrinogen, thrombin or fibrinogen/thrombin mixture prior to producing the FNP by any of the processes described above. Such reactions could be used to trap and cross-link the protein (or hapten) into the entire fibrin matrix from which FNP are fabricated.

EXAMPLE 7

Cell Uptake of FITC-FNP

Figure 2:
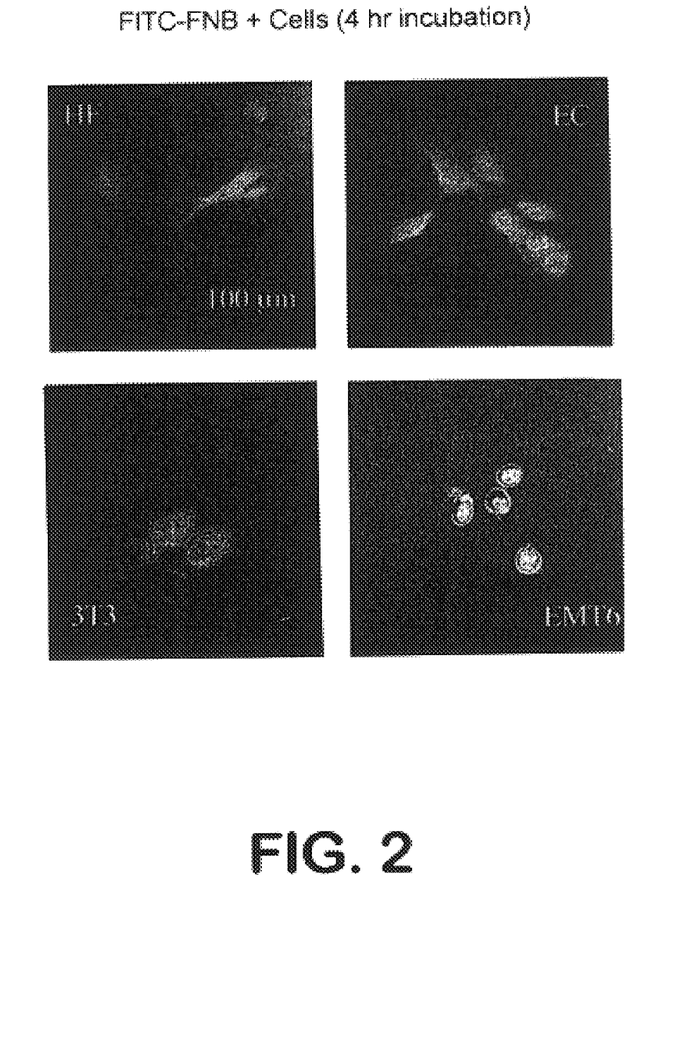
FIG. 2. Fluorescent micrographs showing the uptake of FITC-FNP by 4 cell types after 1 day of incubation. A: Human fibroblasts (HF), B: Bovine endothelial cells (EC), C: 3T3 mouse fibroblast line, D: EMT6 cells. These micrographs demonstrate that derivatized FNP can be adsorbed into the cytoplasm of target cells.

Four different cultured cell types were incubated with FITC-FNP for up to 3 days with aliquots removed and fixed on slides. Light or double (fluorescence and light) by fluorescent microscopy showed that within 1 day, the fluorescent FNP were observed within the cytoplasm of human fibroblasts (HF), bovine endothelial cells (EC), 3T3 fibroblasts and EMT6 cell types (FIG. 2). These results demonstrate that FNP can be derivatized with a protein or hapten and act as carriers for uptake into targeted cells, mostly from mesenchymal origin.

EXAMPLE 8

Isolation of Stem Cells with FMB

Bone marrow (BM) was flushed from the femurs of mice, transferred through needles with serially reduced diameters down to G23 to get mono-cellular suspension. The fresh BM cells (15–20×10⁷ cells/ml) were suspended in 10 ml α-MEM with 20% FCS, 1% antibiotics, 1% glutamine, 1% aminoacids and 1% pyruvate, mixed with 200 µl of packed fibrin microbeads (FMB) 50–100 micron diameter prepared by the Fibrin/Oil process, were suspended in a polycarbonate 50 ml tube. The tube was closed with perforated cap and covered by aluminum foil, to allow gas exchange and placed on a slowly rotating stand (~10 cycles/min) at an angle of ~30°, so that the medium did not reach the perforated cap. After 48 hrs, the unattached cells were separated by brief and mild vortexing and the fibrin microparticle with attached cells (FMB+BM cells) were allowed to sediment for 60–90 sec, the supernatant containing unattached cells was removed, fresh medium was added and the tube was replaced on the rotator in the incubator. Incubation with whole BM resulted in a rapid degradation of the FMB, probably due to the high proteolytic enzymatic and free radical activity of the cell mixture. Thus, the FMB BM cell extraction procedure was limited to 48 hrs.

Figure 3:
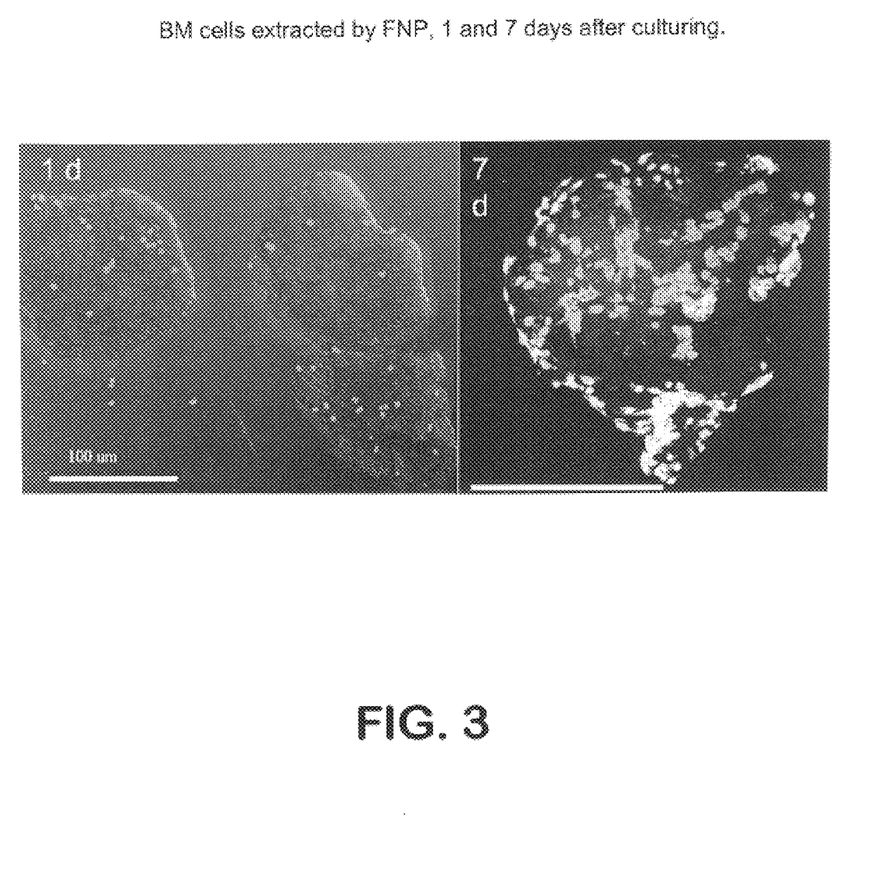
FIG. 3. PI stained cell nuclei of BM derived cells attached to (day 1) and growing on FMB to day 7. Images were composed from multi-sections taken by confocal microscopy. Cells were seen attached on the surface and some penetrating into the FMB.
Figure 4:
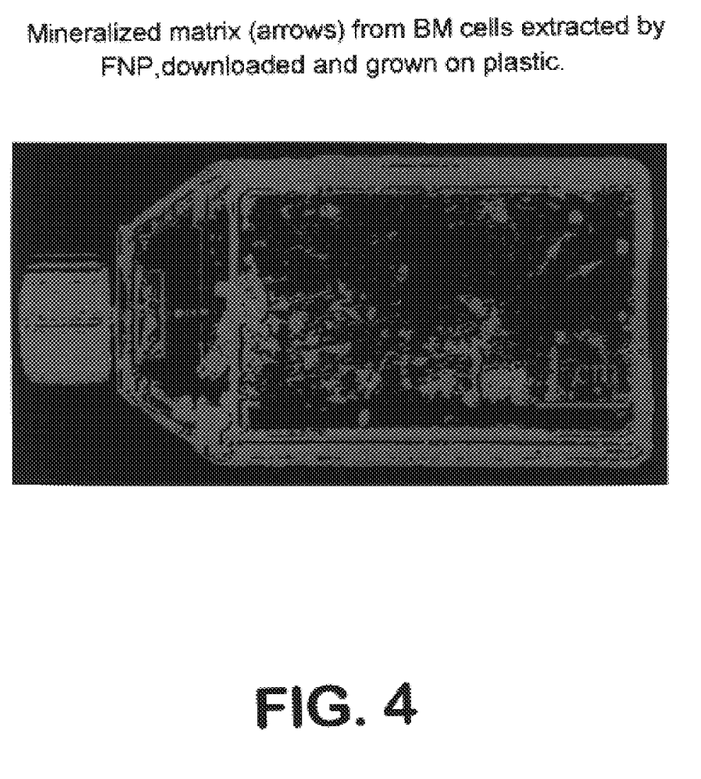
FIG. 4. Induction of ossified islets in vitro by BM cells extracted by FMP produced by method 2, and downloaded onto plastic flasks. After 2 weeks culturing, colony-like foci of osteogenic cells that secreted calcified extracellular matrix were formed.

By confocal microscopy of FMB with propidium iodide (PI) stained cell nuclei, a continued increase of cell number on FMB was observed from day 1 to day 7 (FIG. 3). An aliquot of FMB+BM cells (grown to density of >20×10⁶ cells/ml packed FMB) was washed once with sterile PBS, placed on a plastic flask and incubated in standard condition medium with and without osteogenic supplements. By 3–4 days cells could be seen downloading from the FMB on the plastic surface. About 10 days later, the downloaded cells formed a confluent layer of fibroblast-like cells. In numerous areas, one could observe organized foci (islets) with high cell density, 0.5–4 mm in diameter. In these foci, multi-layers of cells were formed with deposits of opaque extracellular matrix. The addition of a cocktail of osteogenic supplements to the culture medium increased the occurrence and size of such islets. FIG. 4 shows macroscopic large calcified islets seen on the unstained flask as white spots. DXS elemental analysis (Gorodetsky, et al., Direct multi-elemental analysis of platelets in relation to their homologous plasma, as determined by X-ray fluorescence spectrometry. *Am. J. Haematol.* 42: 278, 1993) verified the presence of extremely high levels of Ca in these regions (not shown). These findings indicate that precursor cells from BM extracted with and grown on FMB can be differentiated in vitro into cells with osteogenic properties.

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. Isolated fibrin nanoparticles having a mean diameter of 200–2000 nm.

2. The fibrin nanoparticles of claim 1, having a density of 1.32±0.2 g/ml.

3. A method for preparing fibrin nanoparticles comprising the steps of: (i) mixing an aqueous solution comprising fibrinogen, thrombin and Factor XIII in an oil emulsion at a temperature of 50–80° C., without the addition of an exogenous chemical cross-linking agent, until fibrin microbeads are formed in the mixture; (ii) homogenizing the mixture to form fibrin nanoparticles having a mean diameter of 200–2000 nm in the mixture; and (iii) isolating fibrin nanoparticles having a mean diameter of 200±2000 nm from the mixture.

4. The method of claim 3, wherein the aqueous solution comprising fibrinogen, thrombin and Factor XIII is prepared by contacting thrombin with purified fibrinogen containing endogenous Factor XIII.

5. The method of claim 3, wherein the aqueous solution comprising fibrinogen, thrombin and Factor XIII is prepared by combining thrombin with a cryoprecipitate containing endogenous fibrinogen and endogenous Factor XIII.

6. The method of claim 3, wherein the aqueous solution comprising fibrinogen, thrombin and Factor XIII is prepared by adding separate amounts of fibrinogen, Factor XIII and thrombin.

7. The method of claim 3, wherein ratio of fibrinogen:thrombin:Factor XIII in the aqueous solution is 5–100 mg/mL:1–100 U/mL:1–50 U/mL.

8. The method of claim 3, wherein ratio of fibrinogen:thrombin:Factor XIII in the aqueous solution is 20–40 mg/mL:5–10 U/mL:2–20 U/mL.

9. The method of claim 3, wherein the aqueous solution further comprises at least one agent.

10. The method of claim 9, wherein the agent is a drug, protein, peptide, nucleic acid, saccharide, antigen, hapten, alginate, biodegradable polymer, polyethylene glycol or sugar.

11. The method of claim 3, wherein the aqueous solution comprising fibrinogen, Factor XIII and thrombin is introduced into the oil within about 30 seconds after preparing the aqueous solution.

12. The method of claim 3, wherein the oil in the oil emulsion is selected from the group consisting of corn oil, olive oil, soy oil, castor oil, mineral oil and combinations thereof.

13. The method of claim 12, wherein the oil is corn oil.

14. The method of claim 3, wherein the mixture in step (i) is mixed for about 3–9 hours.

15. The method of claim 3, wherein the fibrin nanoparticles having a mean diameter of 200–2000 nm are isolated by filtration and sedimentation.

16. The method of claim 3, wherein the fibrin nanoparticles isolated in step (iii) have a density of 1.32±0.2 g/mL.

* * * * *

UNITED STATES PATENT AND TRADEMARK OFFICE
CERTIFICATE OF CORRECTION

PATENT NO. : 6,552,172 B2
DATED : April 22, 2003
INVENTOR(S) : Gerard Marx and Raphael Gorodetsky It is certified that error appears in the above-identified patent and that said Letters Patent is hereby corrected as shown below:

<u>Title page,</u>
Item [73], Assignee, "Hapto Biotech, Inc." should read -- HAPTO Biotech, Inc. --

Signed and Sealed this

Twenty-second Day of July, 2003

JAMES E. ROGAN
*Director of the United States Patent and Trademark Office*